United States Patent [19]
Taylor

[11] Patent Number: 5,916,744
[45] Date of Patent: Jun. 29, 1999

[54] **TESTING FOR INFESTATION OF RAPESEED AND OTHER CRUCIFERAE BY THE FUNGUS *LEPTOSPHAERIA MACULANS* (BLACKLEG INFESTATION)**

[75] Inventor: Janet L. Taylor, Saskatchewan, Canada

[73] Assignee: National Research Council of Canada, Ottawa, Canada

[21] Appl. No.: 08/521,053

[22] PCT Filed: Mar. 14, 1994

[86] PCT No.: PCT/CA94/00130

§ 371 Date: Jun. 5, 1997

§ 102(e) Date: Jun. 5, 1997

[87] PCT Pub. No.: WO94/21788

PCT Pub. Date: Sep. 29, 1994

[30] Foreign Application Priority Data

Mar. 22, 1993 [CA] Canada .................................... 2092115

[51] Int. Cl.$^6$ .............................. C12Q 1/68; C12P 19/34; C07H 21/04
[52] U.S. Cl. .............................. 435/6; 435/91.2; 435/810; 536/23.7; 536/24.32; 536/24.33; 536/25.4; 536/25.41; 935/6; 935/8; 935/77; 935/78
[58] Field of Search ............................... 435/6, 91.2, 810; 536/23.7, 24.32, 24.33, 25.4, 25.41, 6, 8, 77, 78

[56] References Cited

PUBLICATIONS

Taylor et al. Current Genetics. 19:263–277, 1991.
Xue et al. Physiological and Molecular Pathology. 41: 179–188, Sep. 1992.
Wostemeyer et al. Advances in Molecular Genetics. 5: 227–240, Dec. 1992.
Goodwin et al. Applied and Environmental Microbiology. 57:2482–2486, Sep. 1991.

*Primary Examiner*—Carla J. Myers
*Attorney, Agent, or Firm*—J. Wayne Anderson

[57] ABSTRACT

A method of testing for infestation of tissue of rape or other Cruciferea with a virulent strain of *Leptosphaeria maculans*. The method involves isolating DNA of *L. maculans* from the tissue; subjecting the isolated DNA to amplification by the polymerase chain reaction (PCR) using sets of primers derived from LMR1 [SEQ ID NO:11] (Genbank accession number M77515), a repetitive element of *L. maculans* specific to virulent strains of the fungus, to form a product containing amplified *L. maculans* DNA; preferably separating the amplified *L. maculans* DNA from the product; and detecting the presence of the amplified separated *L. maculans* DNA. The invention also relates to a method of deriving DNA of *L. maculans* from plant tissue for amplification by PCR, to the oligonucleotides forming the primers used in the PCR and to a diagnostic test kit which makes use of the method of testing.

14 Claims, 2 Drawing Sheets

```
                         SEQUENCE LISTING (1) GENERAL INFORMATION:

(iii) NUMBER OF SEQUENCES:11

(2) INFORMATION FOR SEQ ID NO:1:

(i) SEQUENCE CHARACTERISTICS:
         (A) LENGTH:    24 base pairs
         (B) TYPE:      nucleic acid
         (C) STRANDEDNESS:  single
         (D) TOPOLOGY: linear (xi) SEQUENCE DESCRIPTION:    SEQ ID NO:1:

GCGCTATTAC ACATGCCTAA CAGG                                              24

(2) INFORMATION FOR SEQ ID NO:2:

(i) SEQUENCE CHARACTERISTICS:
         (A) LENGTH:    24 base pairs
         (B) TYPE:      nucleic acid
         (C) STRANDEDNESS:  single
         (D) TOPOLOGY: linear (xi) SEQUENCE DESCRIPTION:    SEQ ID NO:2:

TCCTCTATGC TAAGCTAGCT GTGC                                              24

(2) INFORMATION FOR SEQ ID NO:3:

(i) SEQUENCE CHARACTERISTICS:
         (A) LENGTH:    24 base pairs
         (B) TYPE:      nucleic acid
         (C) STRANDEDNESS:  single
         (D) TOPOLOGY: linear (xi) SEQUENCE DESCRIPTION:    SEQ ID NO:3:

TACTAGGAGG CTCTATAAGT GCGG                                              24

(2) INFORMATION FOR SEQ ID NO:4:

(i) SEQUENCE CHARACTERISTICS:
         (A) LENGTH:    24 base pairs
         (B) TYPE:      nucleic acid
         (C) STRANDEDNESS:  single
         (D) TOPOLOGY: linear (xi) SEQUENCE DESCRIPTION:    SEQ ID NO:4:
```

```
AAGGTATTAG GAGAGCTAGG AGGC                                              24

(2) INFORMATION FOR SEQ ID NO:5:

(i) SEQUENCE CHARACTERISTICS:
         (A) LENGTH:    24 base pairs
         (B) TYPE:      nucleic acid
         (C) STRANDEDNESS: single
         (D) TOPOLOGY: linear (xi) SEQUENCE DESCRIPTION:    SEQ ID NO:5:

GCCTCCTAGC TCTCCTAATA CCTT                                              24

(2) INFORMATION FOR SEQ ID NO:6:

(i) SEQUENCE CHARACTERISTICS:
         (A) LENGTH:    24 base pairs
         (B) TYPE:      nucleic acid
         (C) STRANDEDNESS: single
         (D) TOPOLOGY: linear (xi) SEQUENCE DESCRIPTION:    SEQ ID NO:6:

CTAGCAAGGA AGTAGGCAGG TAAG                                              24

(2) INFORMATION FOR SEQ ID NO:7:

(i) SEQUENCE CHARACTERISTICS:
         (A) LENGTH:    24 base pairs
         (B) TYPE:      nucleic acid
         (C) STRANDEDNESS: single
         (D) TOPOLOGY: linear (xi) SEQUENCE DESCRIPTION:    SEQ ID NO:7:

GCGTAAGAAG CGTGCCTTAG AGTC                                              24

(2) INFORMATION FOR SEQ ID NO:8:

(i) SEQUENCE CHARACTERISTICS:
         (A) LENGTH:    24 base pairs
         (B) TYPE:      nucleic acid
         (C) STRANDEDNESS: single
         (D) TOPOLOGY: linear (xi) SEQUENCE DESCRIPTION:    SEQ ID NO:8:

TCCTGCTCCT ACTCCTTCTC TAGC                                              24

(2) INFORMATION FOR SEQ ID NO:9:

(i) SEQUENCE CHARACTERISTICS:
         (A) LENGTH:    24 base pairs
         (B) TYPE:      nucleic acid
         (C) STRANDEDNESS: single
         (D) TOPOLOGY: linear (xi) SEQUENCE DESCRIPTION:    SEQ ID NO:9:

GGTAGAGCTA GAGGAGGTAG ATAA                                              24

(2) INFORMATION FOR SEQ ID NO:10:

(i) SEQUENCE CHARACTERISTICS:
         (A) LENGTH:    24 base pairs
         (B) TYPE:      nucleic acid
         (C) STRANDEDNESS: single
         (D) TOPOLOGY: linear (xi) SEQUENCE DESCRIPTION:    SEQ ID NO:10:

GCACTTATAG AGCCTCCTAG TAGT                                              24
```

(2) INFORMATION FOR SEQ ID NO:11:

(i) SEQUENCE CHARACTERISTICS:
        (A) LENGTH:    5238 base pairs
        (B) TYPE:      nucleic acid
        (C) STRANDEDNESS: double
        (D) TOPOLOGY: linear (xi) SEQUENCE DESCRIPTION:    SEQ ID NO:11:

```
GGATCCTACC TATAGAAACC TCCTAAATAC AAAAACGTTA TTAAAGCTTA GACTAATACA      60

GGTAACAAGC TTACTACTAC TTAATAATTA GAGATTAAGA AAAGATTAA TAGGAATTAA      120

AAATTTAAAG AGTTAAGAAA AGCTCTAATC AAGTCCTATC CTATTAATCA AGATTATAGT     180

AGTAAGGTAA GCGCGATCAC CTATCTAGGT AGTATCTAGG CAGCACTAAT TAACCCTATA     240

TTAATAGCGG AGAAAACAAA CAGGATCTAT TTAACTATAG ACTTTAAAGC TAACGCTCTA     300

TTAAAGAGCA CTATCTTTAA TAATAGGGGT GCAGTACACC TAGTTAATAA TATAAGCTAC     360

CTAGAAGAAA GCTTGTTTAG ATTAGTTAAA TATAAGATAG TTAAAGTAGG AACTTAAGCT     420

TTTCTAATCT TAGGCAGAGG GACTAGAGTA ATCCCTAATA CTCTTAATAG ACTAAGAGGT     480

CCAAAAACAG AAGATTTAGT GCTTACTAAC GTGGTGTTAG TAGAAGGTTT TTATGTAAAT     540

ATTATATTAG AAGCTTAATT ACTTAAAGCA GGAGTTTAGT TCCTTAGGCT AGATACCACC     600

TTGTAGTTTG GATTATTAGG AAAGAGCGTT ATATTAGCTA AGTTACTGCG CAAGTTTAAC     660

TTAACTTTCC TAGAATACAA GCCCTCTACC CCTTATTAAA TAATCTAAAG CATAGTGCCT     720

AAACAACCCT AACAATCCTA GACGACTTAC CTAAGACACG ACAGTAAGGA GCTTTAGCAC     780

TAATAATTAG GCTATTTAGG ACCTAAGGCG CTTAAAGCTC TAGTTAAGTT AGCAATAAAT     840

ATTAGGATTA AAGGAACTCC TAGGAGCAAA TACGAGCACT GCGCTATTAC ACATGCCTAA     900

CAGGTTATAT CAAGATAACT AAGGGAAAGA TTACCACGTC TATACTACTA GGTATTATAG     960

GATCTATTTA ACATGCTAAC AGGTATAGCT TATAAGCAAT AGATCTTAGT ATTAAAGTGC    1020

GACTACTTAG GAAAGCTTTA TACCTATCTA CTGTAAGCTA AAAACCTTAA TAAGATTATA    1080

CGGGTGTTTA AAAATTTTAA GAGCTTAATA CTTAACTAAT ATAAGCTTAG CATAGTTAAG    1140

ATTATGCAAG ACAACGACGT TGCAACGCTC CCTTAGCGTG GCAAATCTTG CTTTTAGATC    1200

TAGGTAGCTA ACAATAGTAT TAAAATTAAG AGCTTACCTA TATATACCTA TAAACCTAAT    1260

AGAGGAGCAG AAAGAGTAGG GCAGGAGATT ATAACGAAAT TGATTAAAAT AAGGATTAGT    1320

GCTAACCTAC TAACAAAGCT CTAGCCTAAA ATTATTAAAG TAGCAACTTA GCTCTATAAT    1380

ATAAGCCTAT CTTATGCTTA TAATATAATA TCACCTAATA AAGTGCTAGA TTGTTAGTTT    1440

ACTAGATACT TTAGGTAGTA GCAACTAGAG CAGATAAGGG AGGCAACTAC TAATCTCCAC    1500

CCTAATTAGA GCGGAATATA CGCCTATAGC TATTAAGCTT ACCCCCTTAA TAGAGATTAA    1560

GTAGCTAGGC GTTATAAGAG GGTTTTTAAG GTGAACCCTT AGGGTATAT TAGATATCTA     1620

GTAGGATACA AAGTATCTAA TATATATAGG ATATAGATCC CCTTACTTAA TTAGATTATT    1680

ATAATATAGA ACGTTACCTT TAATAAGGAT CTTTTCTACA AAGAGAAAGA TCTAGAGCAG    1740

CTTTAATAGT TAGAGGCTTA AAAGATAGTT AACGTTATTA GCAAAGATAA GATCTATAAT    1800

ATAGGAGAAG CATATAAAGA GCTTAATATC TTTAATTAGC TTTATATTGC AGCAGAGTAA    1860

TATAAGGAGT CTAGTAAGTA AGGAGGACTA AACCTAGCGC AGGAGCTAGG TGGTAGGGTA    1920

GAGCTAGAGG AGGTAGATAA TTAGGCTAGC TAGCCTAGTA ATTCACAACC CCTAAGCAG     1980

ACACCTCTAG CGTGGGTACT AAGCACAGCT AGCTTAGCAT AGAGGATCTA TACAAAGTCC    2040

CCTAAGCTAA TAGGGCTCTA AACTCCTAAA CTAACACTAG AACTAAACTT TAGTATAGGA    2100
```

-continued

```
GATAAAGGAT CTATACAGGT TATAGATTAG GGTTATACTA CCTAAGATAG TAGTAATCTA      2160

ACTTACTTTA ACGCTATAAT AGGTAGCTCC TAGGAAAGAC CTAGAGGGGA GAGTGCTATT      2220

AGTAGGTTAC TCTATAAGAG CACAGAGATA GGTAAGGGCA CCCTATCTAG CCCTTATAGG      2280

GGTGGTGAGC AGAGCTCCTA GAAAAGTAG AAAACCGCAA GTTAAAGGAC TGCCACTAAT       2340

ATATGTTAGT AAGCAAGCTT AGGGATAGGA CCCTAATAAA CTACTAGGAG GCTCTATAAG     2400

TGCGGGATA TATATAGTAA TAGATCTATT AGATATAGAT CTAATTAGAA ATCCCTTATA      2460

CAATCTTTTA GTATATCCTA AACTAAATAC TATAATCCAC GCTGTGATTA TAGTAGTAAT     2520

AGGGAGCAAA TCCCCTAAAA ACCCTAAAAG AAATACGCAC TAGGACGCTC TATAAAAAGA     2580

GCTAAAACAA TAGAAGGATC TCTATAACTA CTAAATAGGA TAGCAATTTA GAGACGTAGT     2640

ATATAAAGAA ATTAATACTC TACTAAAAGC TAGTACCTAG GAGGAGATTA ATAGGCTAAC     2700

TATAGGAGAG TATCTACTCC TACTTAAATA GGTGTTTATA TACAAGCTTA ATTAGGATAG     2760

TTACCTAATT AAGTGTAAAG CAAGGATAGT AGTAAGAGGA GATCTATAGC TTACTAACTT     2820

AATTTATTTA ACCTACGCAG CTACCCTAGT AGCTTAAACC TTAGGACTA TAATAGCTAT      2880

TAGAGCTAAG TTTAACCTTA AGATATATTA ATATAACGTT GTTAGAGCTT TCCTTAACGC     2940

CTTAAGGGAT TAACACCCTA TAGTTATCTG CAAGCTACCT AAAGGATATT AAATACCTAG     3000

GAAGTGCGTT AAGCTTAAAC AAGCTCTATA TAGACTAAAA GACTTACTAT TATTATAGTA     3060

TAATAAGCTC TTAACTACAC TCTAAGAAAA TAAGCTTATT GCTTCTAAAG AGGAACCATG     3120

CCTATTCTTT AACAGAGATC GCAGTATCTT GTTAATATTC TATATAGACA ATATCCTATC     3180

GCTCTATCAC CAAAACTACG CAAGCTAAGC TTACAAAGTT ATCTAAGCTC TAAAGCAAAG    3240

ATATACTATA GAAGAAAAGG GACCTGTAAG CTAGTTTCTA GGGGTAAGAG TAATCTAGGA    3300

TAGAAAGAGA TAGACAATAA CGCTCGTTTA TAATAAATAC ATTAACAAGA TTACAAAGAA    3360

ATTTAATCTA GTAGAGATAG GAAAATTCCC TACTATACTA CTATTAAGTA AAGATATTAA    3420

AAAGAGCACA GGAGAAGCCA CTAAAAAAGA GATTAAGGAC TATTAGGAGC GCGTTAGATT    3480

AATCCTTTAC ACCTTAATTA TAGTGCGCCC TAATATTACC TATGCAGCCT CCTAGCTCTC    3540

CTAATACCTT ACTAACCTAT CTAAACAACA CTTTAATGCA GTTAATTAAG TAATTATCTA    3600

TCTATACTAA ACTTAATACT AATTAATCTA ATATAGGAAT AGGGATCCTA ATAAGCTTAT    3660

AATATATAGT AATGCGTTAT TTGCTAATAA TATTAATACT TAGCAATTAT TATATAGATA    3720

CCTAATCACG CTCTTTAGAG GACCTATTAT TTAGAAGGCA GCTTAACAAG CAACTGTTAC    3780

TACTTTAACT ACTAAGGCAG AGCTCCTTGC GCTTAAGTAA GTAAGTAAAG AAGCAATAGC    3840

GTTAAAACAG TTTTTAACTA AAATACACCT TACTTTAGAT ACTACCTAGA TAATTAATTG    3900

TAATAATTAA CAAACTATTA GGTTAGTAGT AGGCAATAAT AAAAGGATTA CTACTAAGCT    3960

ACGCTATGTA GATATTTAAA ATATATAGCT TAGATAAGAG TATAAAAAGG GATCTTTCTA    4020

TATTACCTAC TTACCTACTA GTAATATACT AGCTAATAGG CTTACTAAAA ACCTAACTGC    4080

ACAATAATTT ATAAGGTTTA GGGAGCACCT AAAGTTATAT AATAGTAGAG CATATATTAT    4140

ATAGTATTAA TTAAAGTAAG GTAGTATATA AGATCTATTA ATATATAATA TAAGAATAAC    4200

TAACTATAGC CTACCTCTCT ATTATTAACT AGGTAGCTTC CCTAAGGAGC TCTATTACGC    4260

GTAAGAAGCG TGCCTTAGAG TCTATAGGGA GCCGCCTAGG TTGCCCTAAC CTAGAATCTA    4320

TAAGGGGAAC CTTAGAGGAG CTAGAGTCCT TATCTTCTAA TAAGGAGCTC TAGGCGCCCT    4380

TAGCTATAGT ATTAGCCTTG CGCGTAAGCT TAGCAGCAGT AGTAGTACCT TTTACTAGCT    4440

CCTACTATTT AGCCTTGCTC TCCTTAAGGA GCACTAAGAC CCTCTGCTTC TTATCCTTAA    4500
```

```
GAAGGTCTTA GCTCTTACCT GCCTACTTCC TTGCTAGGAA GGATAGCGTA GAATATTAGG    4560

CAAGCTTAGG GCTATTAGTT TGTTAGTATA GATCTTACTA AGCGTTATAA AGGAAAAATT    4620

CTTATATAGA TTATATATAC AGGGATATAG CTATACCTAG AGAAGCACTA CTAGCACTAA    4680

GTCCCCCTAC TAGAAGAGTT ATAGCACTTA CTATTAGACT TATTAAAGAG CGCTAAGTAT    4740

AGATAATTTA GACAAGTTTT AGTATAATAA ATACTAGGCT CTCTATAATA GGAGGATCTT    4800

AGGGTCTCCT TAGGAGCTAG AGAAGGAGTA GGAGCAGGAG TAAGGATAGG GGGCAGGGTC    4860

TAGGGAGGAG CAGGAGCTAG AGTTAGAGCT AGAGTAGTAG AAGCTAGAGT AGAAGCGCCC    4920

TTCCTTAGCT TCGCGATCTT AACTATAGTA GTAGTAGCTA CGTACTTAGC TACTATATAC    4980

TCTATAATAG CCTTACGCTT AGTAGTAGCA CGCTCTTCTT TAGTAGTAGT AGCTTTAGCA    5040

ACTACAGCTT TAGCTACGTA GGAGGTAATA AGGGTAGCGT AGGCAGAGTA AGTGCAAGTA    5100

GTAGGTTTTA ACTTTAACTA AGATATAGGT TAGTAAGGAT ATAAGTATAG TTTAGATCTT    5160

TAGGGTTATA TAATCTTATA ACTTAGGCTA TAGTAAAGAT TATAGTTAGG TAGATAGAGT    5220

TATAGAGCTC TATCTAGA                                                  5238
```

TESTING FOR INFESTATION OF RAPESEED AND OTHER CRUCIFERAE BY THE FUNGUS LEPTOSPHAERIA MACULANS (BLACKLEG INFESTATION)

BACKGROUND OF THE INVENTION

I. Field of the Invention

This invention relates to tests for blackleg contamination of Cruciferae, particularly Brassica spp., and especially oilseed rape or canola. More particularly, the invention relates to the testing of seeds and other products or tissues of such Cruciferae, particularly rapeseed, for contamination by virulent strains of the fungus responsible for causing the disease.

II. Description of the Prior Art

In the central region of the western Canadian province of Saskatchewan, the disease of blackleg of oilseed rape (*Brassica napus* and *Brassica rapa*) has spread from three widely spaced fields in 1975 to almost 90% of the land cultivated with this crop in 1988 and the disease represents a loss in crop yield worth millions of dollars per year. While blackleg infestation can be spread by infested crop residue or plants, the disease is commonly seed-borne and this fact places a considerable responsibility on seed growers to test their seed for absence of the blackleg fungus in order to prevent the spread of the disease to currently uninfected areas.

The introduction of more tolerant varieties of rape has greatly reduced the incidence of the disease in Europe. However, for cold winter climates, such species are not suitably viable and crop rotation is still the most effective means of controlling the disease, so preventing the introduction of the fungus into rapeseed growing areas has primary importance.

The disease is caused by *Leptosphaeria maculans* (Desm.) Ces. et de Not. [anamorph: *Phoma lingam* (Tode: Fr.) Desm.], a hetrothallic ascomycete. The blackleg fungus exists in western North America in two forms: weakly virulent (non-aggressive) strains and virulent (severe or highly virulent, aggressive) strains. It is the virulent strains that cause substantial damage to rapeseed (canola) crops and other Cruciferae. The weakly virulent strains cause only mild disease symptoms with no substantial yield loss and their presence in seed is not a matter of serious concern. These strains look similar in culture and can only be differentiated by specialized tests. For example, the 2,4-D blotter method recommended by the International Seed Testing Association cannot differentiate between the weakly and highly virulent isolates. G. A. Petrie has developed a test for differentiating the strains of the fungus (see "The rapid differentiation of virulent and weakly virulent strains of *Leptosphaera maculans* (blackleg or stem canker) and related pycnidial fungi from Brassica seeds and stems", Canadian Journal of Plant Pathology, 10:188–190, 1988), but this test is based on differences in germ tube length after incubation and is not very convenient.

There is therefore an increasing need for a relatively simple and reliable test for detecting infestations of blackleg of oilseed rape and other Cruciferae, and particularly one which can distinguish the highly virulent strains from the weakly virulent strains.

OBJECTS OF THE INVENTION

An object of the present invention is therefore to simplify testing for the blackleg fungus.

Another object of the invention is to provide a test for the blackleg fungus that can distinguish between the weakly virulent and highly virulent strains of the fungus.

Yet another object of the invention is to develop a test for the blackleg fungus that can be carried out relatively quickly and easily using relatively simple equipment.

A still further object of the invention is to provide a diagnostic test kit for testing for infestations of the blackleg fungus.

SUMMARY OF THE INVENTION

In a primary aspect; the invention relates to a method of testing for infestation with a virulent strain of the fungus *Leptosphaeria maculans* (*L. maculans*) of tissue of rape or other Cruciferae. The method comprises isolating DNA of a virulent strain of *L. maculans* from the issue; subjecting the isolated DNA to amplification by polymerase chain reaction (PCR) using effective primers derived from LMR1 [SEQ ID NO:11] (Genbank accession number M77515), a repetitive element of *L. maculans* specific to virulent strains of the fungus, to form a product containing amplified *L. maculans* DNA in sufficient quantity for detection; and detecting the presence of the amplified *L. maculans* DNA. Normally, the amplified *L. maculans* DNA is separated from the product before the detection of the DNA is carried out.

The invention also relates to a method of deriving DNA of *L. maculans* from plant tissue for amplification by PCR, to the primers used for the amplification and to diagnostic test kits which make use of the method of testing.

The detection method of the present invention generally requires less than one half the time required for conventional testing methods and does not require the plating of individual seeds. The method can therefore be used to screen larger sample sizes.

The method has been found to be about 73% reliable in the tests carried out so far (which is acceptable for this type of test) and highly sensitive (the method successfully detected the minimum contamination level that was tested (0.4%), i.e. as little as one contaminated seed out of 1000 uncontaminated seeds).

BRIEF DESCRIPTION OF THE DRAWINGS

FIG. 1 shows the PCR products from reactions containing 5.0 ng DNA from the virulent *L. maculans* isolate Leroy amplified with five different sets of primers as shown in Table 1 below. The lanes, left to right, 1 kb ladder, show: (1) primer set A, 1145 bp; (2) primer set B, 1168 bp; (3) primer set C, 1010 bp; (4) primer set D, 580 bp; and (5) primer set E, 486 bp.

FIG. 2 shows a determination of the minimal amount of DNA from the virulent isolate Leroy amplified by primer set D that leads to a visible product. The amount of DNA added to each reaction is stated beside the lane number. The lanes, left to right, one kb ladder, show: (1) 5.0 ng; (2) 2.5 ng; (3) 1.0 ng; (4) 100 pg; (5) 10 pg; (6) 1.0 pg; (7) 100 fg; (8) 10 fg; (9) 1.0 fg; and (10) O.

FIG. 3 shows the effects that the length of seed culturing, culture medium, and DNA isolation procedure, respectively, have on the amount of the amplification product. One hundred nanograms of DNA and primer set D were added to each reaction and the factors not under study were at their optimum. The lanes, left to right, 1 kb ladder, show: (1) 48 h; (2) 72 h; (3) potato dextrose broth; (4) minimal medium;

(5) ethanol used in the initial DNA precipitation; (6) cetyl trimethylammonium bromide (CTAB) used in the initial DNA precipitation.

Figure 1:
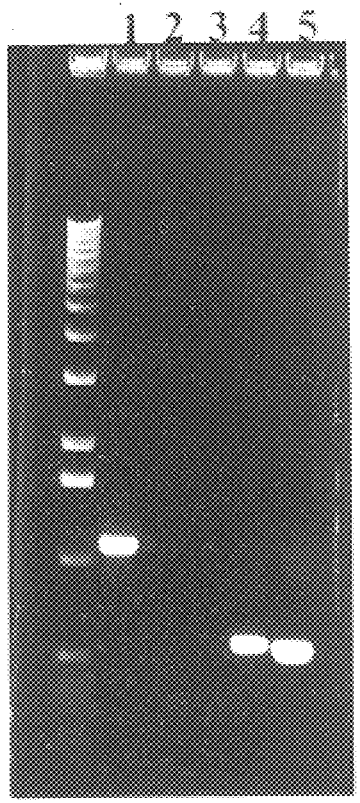
FIGS. 1–4 show electrophoresis gels of products of reactions explained in the Examples.
Figure 2:
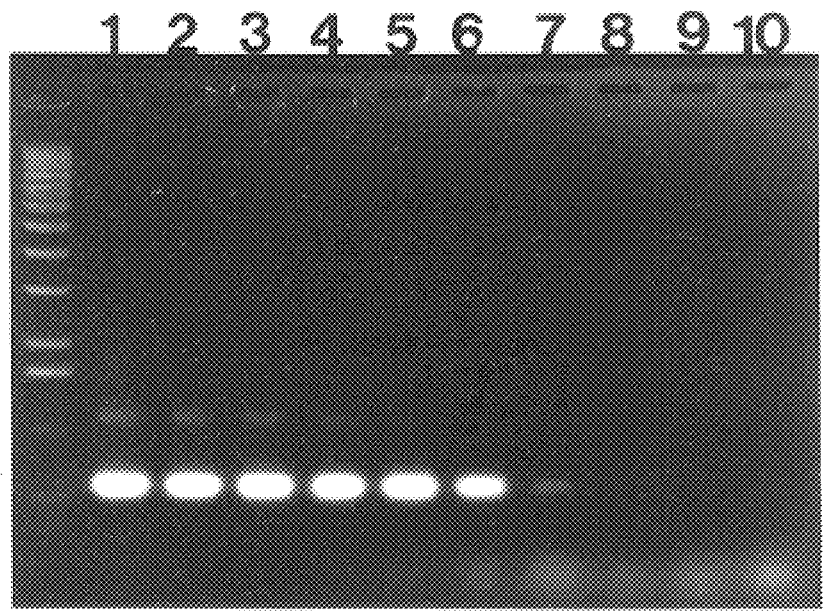
Figure 3:
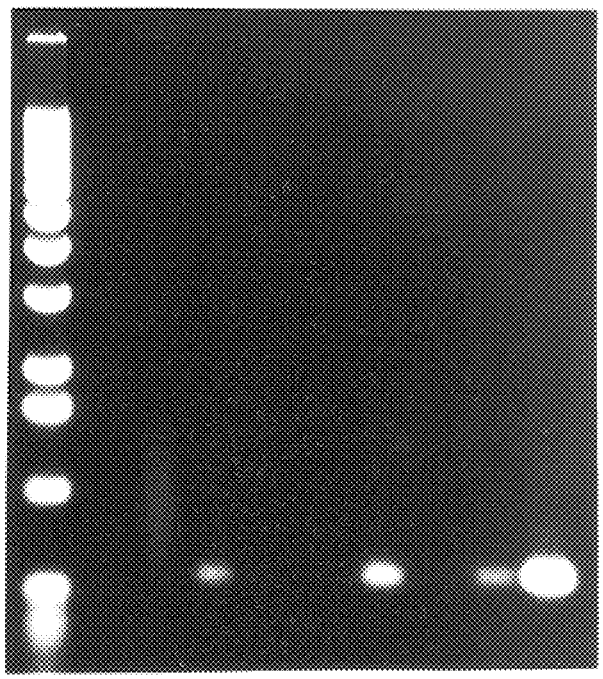
Figure 4:
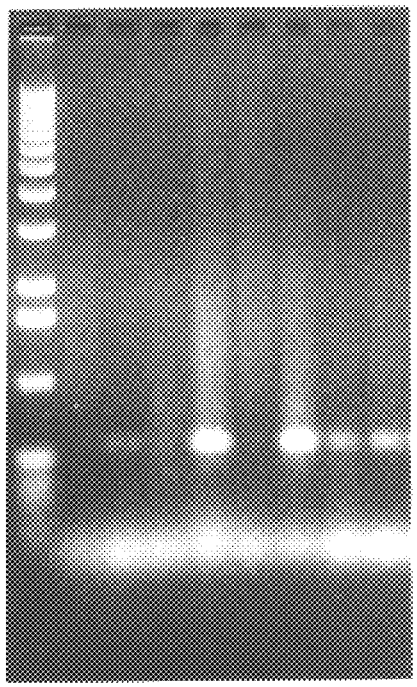

FIG. 4 provides an assessment of the detection levels of the PCR-based seed contamination test. Varying amounts of seed from the 1–2% contamination lot were mixed with uncontaminated seed to a total of 2.0 g, and cultured for DNA isolation. The amount of the contaminated seed lot added to the uncontaminated lot, the estimated number of seed contained in that amount, and the estimated maximum number of contaminated seed present are given in that order beside the lane number. The lanes, left to right, 1 kb ladder, show: (1) 0 g, 0, 0; (2) 0.1 g, 50, 2; (3) 0.25 g, 125, 4; (4) 0.5 g, 250, 6; (5) 0.75 g, 375, 8; (6) 1.0 g, 500, 10; (7) 1.5 g, 750, 16; and (8) 2.0 g, 1000, 20.

DETAILED DESCRIPTION OF THE PREFERRED EMBODIMENTS

The present invention makes use of the polymerase chain reaction (PCR) to amplify relatively small amounts of DNA segments of L. maculans that are specific to the virulent strains so that the presence of this DNA can be easily detected by known methods. To make it possible to use the PCR for such a test procedure, it was first necessary to develop a procedure for effectively isolating blackleg fungal DNA from plant tissue, such as seeds, and to provide oligonucleotide primers specific to the virulent strains of the fungus.

The preferred method of isolating the fungal DNA from seed (or other plant) tissue involves placing surface-disinfested seed in liquid fungal minimal medium, shaking the culture for a suitable period of time (usually at least 3 days) at ambient temperature and collecting the fungal mycelia from the medium by centrifugation. The mycelia may then be lysed by a suitable medium (e.g. by using a combination of sodium dodecyl sulfate and proteinase K) and the DNA extracted with organic solvents and precipitated with cetyl trimethylammonium bromide. This procedure provides sufficient target DNA for PCR amplification and subsequent detection of the target DNA.

Fungal minimal medium is a nutrient solution containing the minimal ingredients for fungal growth. Fungal minimal medium differs from a bacterial medium mainly in the identity of the nitrogen source. Bacteria require a reduced form of nitrogen as in $NH_4^+$, while fungi can use $NO_3^-$. Thus fungal minimal medium contains $NO_3^-$ or the equivalent as the principal nitrogen ingredient. This discourages the growth of bacteria instead of the desired fungus. Other nutrients are also kept to a minimum for the same reason since otherwise bacterial growth may take over. The other ingredients can be selected and their amounts determined to satisfy the minimal nutrient requirements of the fungus.

The polymerase chain reaction is a known technique which makes it possible to detect the presence of particular DNA sequences in a background of unrelated nucleotide sequences. The technique is described, for example, by R. K. Saiki et. al. in "Primer-Directed Amplification of DNA with a thermostable DNA Polymerase", Science, 239:487–491 (1988) (the disclosure of which is incorporated herein by reference). The technique is a method of amplifying DNA sequences a few hundred bases long by over a million-fold without using methods of genetic manipulation that require the use of biological vectors. The method makes use of two oligonucleotide primers which flank the sequence to be amplified but which bind to opposite strands. In a typical procedure, a cycle involves first denaturing the target DNA (and later the synthesized polynucleotide) at high temperature (e.g. about 90° C. or higher), then annealing the primers to the denatured DNA at lower temperature (e.g. about 50° C.), followed by reaction with a thermostable polymerase (e.g. a polymerase isolated from the bacterium Thermus aquaticus or the Taq polymerase commercially available from companies supplying enzymes for molecular biology, e.g. Life Technologies of Gaithersburg, Md, USA) at an intermediate temperature (e.g. about 70° C.). This cycle is repeated usually about 20 to 40 times, each cycle approximately doubling the amount of target DNA.

The primers employed in the process of the invention are derived from a 5238 base pair (bp) repetitive sequence known as LMR1 [SEQ ID NO:11] present in approximately 80 copies per haploid genome only in virulent isolates of L. maculans (e.g. as in the highly virulent isolate "Leroy", obtainable from R. K. Gugel, Agriculture Canada Research Station, Saskatoon, Saskatchewan, Canada and deposited under deposit number DAOM194208 in the culture collection of the Center for Land and Biological Resources, Ottawa, Ontario, Canada). LMR1 [SEQ ID NO:11] is present on every chomosome of the virulent strains, although not in equal copy numbers and it is speculated that the element may be attached to genes involved in pathogenicity.

Repetitive DNA sequences are a common feature of both prokaryotic and eukaryotic genomes and their function has given rise to much speculation and research without a clear and unequivocal explanation. However, it has been found that this particular repetitive sequences of L. maculans can be used to distinguish the virulent strains from the weakly virulent strains.

The LMR1 [SEQ ID NO:11] element was identified by constructing a lambda-genomic library of DNA from the LEROY isolate and screening it with radiolabelled genomic DNA. A clone which contained 14 kilobases (kb) of fungal DNA that hybridized very strongly was isolated. It was established that a 5.2 kb segment of that DNA is present in multiple copies in all of 14 highly virulent isolates that were examined and is virtually undetectable in weakly virulent isolates. In addition, no cross hybridization of the fungal DNA to rapeseed DNA sequences was detected.

The sequence of the LMR1 [SEQ ID NO:11] element was recorded in the database of Genbank, Los Alamos National Laboratory, Group T-10, Theoretical Biology and Biophysics, Mail Stop K710, Los Alamos, N.Mex, U.S.A. (telephone 505 665-2177) on Sep. 13, 1991 and is freely available under accession number M77515. The full sequence of the LMR1 [SEQ ID NO:11] element is provided in the Sequence Listing at the end of this disclosure, which Sequence Listing forms part of this application.

The LMR1 [SEQ ID NO:11] element hybridizes, under stringent conditions, to every virulent isolate of the fungus examined but not to any weakly virulent isolates and its high copy number per genome increases the probability of obtaining a visible amplification product from a small amount of input DNA.

The LMR1 [SEQ ID NO:11] element provides a large resource for specific primer selection, which can be carried out using only the sequence information provided in the Sequence Listing, i.e. there is no need to obtain the element itself for primer selection. The initial selection can be carried out by means of specially designed computer programs, e.g. "The Primer Designer™", from Scientific & Educational Software, that utilize the following general principles for selection: about 20–25 bases including 5' extension, pairs of primers should be less than 2 kb apart, % GC=50–60, Tm° C.=55–80, and rejection of the following in primers: runs of 3 bases or more, secondary structure, 3 or more G or C at the 3' end, primer interactions involving the 3' end and extensive homology. Pairs of primers for use together should of course have no extensive pairing interactions with each other. Using these criteria, it is possible to select primers corresponding to any part of the LMR1 [SEQ ID NO:11] sequence.

The primers identified in this way can then be chemically synthesized by well-known techniques for producing short sections of DNA, e.g. by means of solid phase phosphite-triester oligodeoxyribonucleotide synthesis. Such syntheses can be performed manually or using commercially available gene synthesizing machines (e.g. an Applied Biosystems 370A sequencer using the Taq Dye Deoxy Terminator cycle system). Syntheses of this type are so commonly performed nowdays by molecular biologists and biochemists that no further details are believed to be necessary to enable the application of such techniques to the present invention.

Pairs (referred to as "sets") of DNA sequences that were identifed and synthesized in this way as possibly effective primers are shown in Table 1 below:

tation with the virulent strains of the fungus, for example *Brassica juncea*.

The present invention also relates to diagnostic kits for testing for infestation of Cruceferae plant tissue, particularly rape seed, with virulent strains of *L. maculans*. Such kits may comprise a solution of the primers, a PCR buffer, a heat-resistant polymerase (e.g. Taq), a solution of deoxynucleotides and DNA from a highly virulent strain of *L. maculans* and a weakly virulent strain of *L. maculans* (to act as controls). The kit would also normally include instructions for use in conjunction with a thermal cycler that would not normally form part of the kit.

The invention is illustrated further by the following Examples, which are not intended to limit the scope of the invention.

EXAMPLES

I. Extraction of Fungal DNA

The highly virulent *L. maculans* isolate "Leroy" was obtained from R. K. Gugel (Agriculture Canada Research Station, Saskatoon, Saskatchewan, Canada). The isolate was cultured on plates on V8 juice agar containing 200 ml of

TABLE 1

| SET | SEQUENCE | SEQ. ID. NO. | LMR1 [SEQ ID NO: 11] BP POSITION | EXPECTED SIZE BP |
|---|---|---|---|---|
| A | 5'-GCGCTATTACACATGCCTAACAGG-3' | [SEQ ID NO: 1] | 881 | 145 |
|   | 5'-TCCTCTATGCTAAGCTAGCTGTGC-3' | [SEQ ID NO: 2] | 2026C |  |
| B | 5'-TACTAGGAGGCTCTATAAGTGCGG-3' | [SEQ ID NO: 3] | 2382 | 1168 |
|   | 5'-AAGGTATTAGGAGAGCTAGGAGGC-3' | [SEQ ID NO: 4] | 3550C |  |
| C | 5'-GCCTCCTAGCTCTCCTAATACCTT-3' | [SEQ ID NO: 5] | 3527 | 1010 |
|   | 5'-CTAGCAAGGAAGTAGGCAGGTAAG-3' | [SEQ ID NO: 6] | 4537C |  |
| D | 5'-GCGTAAGAAGCGTGCCTTAGAGTC-3' | [SEQ ID NO: 7] | 4259 | 580 |
|   | 5'-TCCTGCTCCTACTCCTTCTCTAGC-3' | [SEQ ID NO: 8] | 4839C |  |
| E | 5'-GGTAGAGCTAGAGGAGGTAGATAA-3' | [SEQ ID NO: 9] | 1917 | 486 |
|   | 5'-GCACTTATAGAGCCTCCTAGTAGT-3' | [SEQ ID NO: 10] | 2403C |  |

These primers are each 24 nucleotides in length, have a minimum GC content of 45%, a minimum Tm of 67° C. and amplify fragments of approximately 1.0 kb or less. The sequence of the primers, their starting bp positions in the LMR1 [SEQ ID NO:11] sequence and the size of the expected amplification product are shown in Table 1 above. Of the above sets, sets A, D and E have been found to be effective and set D is the most preferred. Sets B and C do not work effectively and thus are not considered to be effective primers. They are provided merely for comparison. It should be noted that "effective primers" are those that have not only been selected and synthesized in the manner indicated above, but also tested in the PCR and found to duplicate fungal DNA sequences in amounts that can be readily and reliably detected.

Once the target DNA has been amplified using the indicated primers in the PCR, the amplified DNA is preferably separated from the PCR product, e.g. by conventional horizontal agarose gel electrophoresis, and detected, e.g. by being stained for photography with a suitable compound, such as ethidium bromide.

While the method of the invention is primarily intended for the testing of seed for infestation with the fungus, it can be applied to the testing of any plant tissue or material containing small amounts of fungal DNA. Rape is the primary crop of interest for testing, but other Cruciferae may be tested in the same way if they are susceptible to infescommercial mixed vegetable juices sold under the trademark "V8", 800 ml of distilled water, 0.75 g $CaCO_3$, 10 ml of rose bengal (4% solution) and 15 g agar, which was autoclaved at 121° C. under 20 lbs. pressure for 20 minutes, allowed to cool to 55° C., followed by adding 2 ml of sterile streptomycin sulfate (5% solution).

For DNA isolation, plugs from the plates were transferred to liquid fungal minimal medium and grown for one week at room temperature with shaking. The minimal medium used in all the described experiments contained 3.12 g/L $KNO_3$, 0.75 g/L $K_2HPO_4$, 0.75 g/L $KH_2PO_4$, 0.1 g/L NaCl, 0.28 g/L asparagine, 0.1 g/L $CaCl_2$.2 $H_2O$, 0.5 g/L $MgSO_4$.7 $H_2O$, 0.4 mg/L $ZnSO_4$.7 $H_2O$, 79 µg/L $CuSO_4$.5 $H_2O$, 41 µg/L $MnSO_4$.4 $H_2O$, 18 µg/L $MoO_3$ (85%), 0.5 mg/L $FeC_6H_5O_7$, 38 µg/L $Na_2B_4O_7$, 10 $H_2O$, 0.1 mg/L thiamine and 15 g/L glucose, pH adjusted to 6.55.

Two different seed lots of the *B. napus* rapeseed variety Tristar were obtained from R. K. Gugel (see address above). Both seed lots were tested for blackleg contamination using conventional methods. One lot grown in California was found to be free of blackleg contamination and the second lot grown in Saskatchewan was found to contain 1–2 contaminated seeds/100 seeds.

The mycelium of the fungal isolate was collected by filtration, freeze-dried and vortexed in the presence of glass beads. The DNA was extracted from the resulting powder by a modified method according to Murray and Thompson, "Rapid isolation of High Molecular Weight Plant DNA", Nucl. Acids. Res. 8:4321–4325.

The DNA from the surface of germinating *B. napus* seed was isolated in the following manner. The seed was surface-disinfested by soaking in 1.0% (v/v) NaOCl (6.0% available chlorine) for 15 min. and rinsed in sterile deionized water. Two to five grams of seed was added to 50 ml fungal minimal medium and cultured for 72 h at 26±2° C. with shaking. The medium was poured through two layers of sterile cheesecloth into centrifuge tubes and centrifuged at 2500×g for 10 min. The pellets were washed twice with sterile $H_2O$, the second wash was carried out in microfuge tubes. The pellets were dried overnight in a speed-vac (Savant Instruments, Farmingdale, N.Y.) and resuspended in 10 mM Tris-HCl, pH 7.8; 5 mM EDTA; 0.5% sodium dodecyl sulfate (SDS). Proteinase K (Sigma) was added to a final concentration of 100 µg/ml and the samples were incubated at 56° C. for 4 h. The samples were extracted once each with phenol, phenol-chloroform, and chloroform. The DNA was precipitated by adding an equal volume of 50 mM Tris-HCl, pH 8.0; 10 mM EDTA; 1.0% CTAB (cetyltrimethylammonium bromide), followed immediately by centrifugation at 12,000×g for 30 min. The pellets were dried, resuspended in 1.2M NaCl and re-precipitated with ethanol. The DNA was resuspended in 10 mM Tris-HCl, pH 8.0; 1 mM EDTA (referred to as "TE") and treated at 37° C. for 1 h with RNase A (50 µg/ml) and RNase T1(200 units/ml). The DNA was extracted once with phenol-chloroform and precipitated with ethanol. The DNA was resuspended in TE and the concentration was measured by absorbance at 260 nm.

II. DNA Amplification by PCR

Five nanograms purified fungal DNA, unless otherwise stated, or 100 ng seed derived DNA was added to each of several amplification reactions. The amplification reactions contained 200 µM dNTPs; 165 nM each primer; 20 mM Tris-HCl, pH 8.8; 10 mM KCl, 10 mM $(NH_4)_2SO_4$; 5 mM $MgSO_4$; 0.1 Triton X-100; 27.5 µM tetramethylammonium chloride; and 2.5 units Taq polymerase (Life Technologies). The amplifications were performed in a Barnstead Thermolyne thermal cycler (available from Baxter-Canlab) using the following program. The samples were initially heated to 96° C. and held at that temperature for 2 min, then 35 ramped cycles consisting of 94° C. for 30 s, 71° C. for 30 s, and 72° C., for 4 min were performed and a final extension at 72° C. for 7 min was added.

The primers used in the amplification reactions were derived from the sequence of LMRI (Genbank accession number M77515), a repetitive element found only in virulent isolates of *L. maculans*. The Primer Designer, version 1.0, computer program from Scientific & Educational Software was used to select the optimal primers from the sequence. The primers were chosen to amplify fragments of approximately 1.0 kb or less. The sequence of the primers and their starting bp positions in the LMR1 sequence were as given earlier in Table 1.

The PCR products were run on 0.8% agarose gels in 1× Tris-acetate buffer and stained with ethidium bromide for photography.

III. Results

A. AMPLIFICATION OF LEROY DNA

The primers indicated above were used to amplify 5.0 ng of DNA from the highly virulent isolate Leroy. A photograph of a gel containing the amplification products is shown in FIG. 1. Primer set A (see Table 1 above) amplified primarily a fragment of 1145 bp as expected, a second faint band appeared at approximately 850 bp. The amplification products from primer sets B and C, a 1168 bp and 1010 bp fragment, respectively, were only faintly visible on gels and are not apparent in FIG. 1. The expected 580 bp fragment was the predominant product in amplification reactions containing primer set D. A second faint band appeared at approximately 1200 bp. A large amount of the expected 486 bp fragment was amplified using primer set E. A second product, faintly visible at 1100 bp, was also present in these reactions.

IV. Seed Contamination Test

Primer set D was chosen for use in the development of a seed contamination test. This primer set consistently produced the largest amount of the expected product DNA from the virulent isolates tested and had the least tendency to amplify fragments from DNA from weakly virulent isolates.

In order to determine the minimum detection level of DNA, amplification reactions were carried out with decreasing amounts of Leroy DNA to determine the minimum amount of DNA whose amplification would lead to a visible product on ethidium bromide stained gels. The products from these reactions are shown in FIG. 2. The amounts of fungal DNA that were added to the reactions were (1) 5.0 ng, (2) 2.5 ng, (3) 1.0 ng, (4) 100 pg, (5) 10 pg, (6) 1.0 pg, (7) 100 fg, (8) 10 fg, (9) 1.0 fg, (10) 0. The lowest amount of DNA added to an amplification reaction that led to a visible product was 100 fg. The average size for the genome of a virulent isolate of *L. maculans* has been estimated to be 27.6 Mb. Thus the 100 fg represents the amount of DNA present in as little as four nuclei.

V. Factors Affecting Detection of Contaminated Seed

A number of factors were found to affect the ability to detect a product from amplifications of DNA isolated from germinating seed. These factors included the length of time that the seed was incubated in the fungal medium, the type of medium used, and the DNA preparation procedure. The effects that these various factors had on amplification are shown in FIG. 3. The seed lot used in these assays was found, using the presently employed methods, to contain 1–2% contaminated seed.

One hundred nanograms of DNA, isolated 48 h or 72 h, respectively, after inoculation of 2.0 g of seed into minimal medium, was added to the amplification reactions pictured in lanes 1 and 2. A product of specific size was only present in the reaction that contained DNA isolated after 72 h.

The effect that the type of medium, in which the seed was incubated, had on detection of an amplification product is shown in lanes 3 and 4. One hundred nanograms of DNA isolated 72 h after inoculation of 2.0 g of seed into potato dextrose broth was used in the reaction shown in lane 3. The same amount of DNA isolated after incubation in minimal medium was added to the lane 4 reaction. Only the minimal medium sample gave a visible product. Observation of the medium collected at the end of the incubation time indicated that the potato dextrose broth favored the growth of bacteria over fungi.

The DNA used in the reactions pictured in lanes 5 and 6 was initially precipitated with ethanol or cetyl trimethylammonium bromide (CTAB), respectively, the incubation time and medium were the optimal determined above. A greater amount of product resulted from the use of CTAB precipitated DNA in the reaction.

VI. Sensitivity of the Assay for Seed Contamination

Varying amounts of seed from the lot containing 1–2% contamination were mixed with seed from an uncontaminated lot to determine the sensitivity of the assay. The results are shown in FIG. 4. One hundred nanograms of seed derived DNA, isolated using the optimal conditions described above was added to each reaction. A total of 2.0 g of seed was cultured for each sample, this weight is equal to approximately 1000 seeds. The weight of seed from the contaminated lot mixed with uncontaminated seed and an approximation of the number of seeds from each lot that amount represents is given below.

The DNA amplified in the lane 1 reaction was isolated from 2.0 g (1000 seed) of uncontaminated seed. The lane 2 reaction contained DNA from 0.1 g (50 seed) of the contaminated seed lot mixed with 1.9 g (950 seed) uncontaminated seed lot. This would represent a maximum of 2 contaminated seed out of the 1000. The lanes 3–8 reactions used DNA from cultures of 0.25 g (125), 0.5 g (250), 0.75 g (375), 1.0 g (500), 1.5 g (750), 2.0 g (1000), respectively, of contaminated seed lot mixed with the appropriate amounts of uncontaminated to make a total of 2.0 g seed. The estimated maximum number of contaminated seed that these amounts represent ranges from 4 to 20 out of 1000. The reactions that contained DNA from the 0.25 g and 0.75 g cultures had only faintly visible bands and the bands produced from 1.5 g and 2.0 g cultures were less intense than those in the 0.5 g and 1.0 g reactions. This sample to sample variation was common and consistently found in different sample preparations. A decrease in band intensity was observed when the same DNA sample was used in amplifications over several successive days. Thus the most likely explanation for the sample variation is a difference in the degree of contamination of the samples with nucleases.

What we claim is:

1. A method of testing for infestation of tissue of rape or other Cruciferae with a virulent strain of the fungus Leptosphaeria maculans (L. maculans), comprising:
   isolating DNA of a virulent strain of L. maculans from the tissue;
   subjecting the isolated DNA to amplification by polymerase chain reaction using oligonucleotide primers which specifically hybridize to LMR1 [SEQ ID NO:11], said primers being effective to amplify said DNA in quantities suitable for detection; and
   detecting the presence of said amplified L. maculans DNA as indicative of infestation with a virulent strain of L. maculans.

2. A method according to claim 1 wherein said polymerase chain reaction produces a reaction mixture and said amplified DNA is separated from said mixture prior to detecting the presence of said DNA.

3. A method according to claim 1 comprising employing a set of primers for said polymerase chain reaction having the following criteria: (a) each primer has about 20–25 bases, including 5' extensions; (b) the primers of said set are derived from sequences of DNA of LMR1 [SEQ ID NO:11] less than 2 kb apart; (c) the amount of GC in the primers is 50–60%; (d) the Tm° C. of the primers is 55–80; and (e) the primers do not contain or show runs of three or more identical bases, secondary structures, three or more G or C at the 3' ends, primer interactions involving the 3' ends and extensive homology.

4. A method according to claim 1 comprising employing sets of primers for the polymerase chain reaction selected from the group consisting of:
   (A) 5'-GCGCTATTACACATGCCTAACAGG-3' [SEQ ID NO:1],
   5'-TCCTCTATGCTAAGCTAGCTGTGC-3' [SEQ ID NO:2];
   (D) 5'-GCGTAAGAAGCGTGCCTTAGAGTC-3' [SEQ ID NO.7],
   5'-TCCTGCTCCTACTCCTTCTCTAGC-3' [SEQ ID NO.8];
   and
   (E) 5'-GGTAGAGCTAGAGGAGGTAGATAA-3' [SEQ ID NO:9],
   5'-GCACTTATAGAGCCTCCTAGTAGT-3' [SEQ ID NO:10].

5. A method according to claim 1 comprising employing for the polymerase chain reaction the following set of primers:
   (D) 5'-GCGTAAGAAGCGTGCCTTAGAGTC-3' [SEQ ID NO:7],
   5'-TCCTGCTCCTACTCCTTCTCTAGC-3' [SEQ ID NO:8].

6. A method according to claim 1 comprising isolating said DNA of said virulent strain from the tissue by:
   placing surface-disinfested tissue in liquid fungal minimal medium,
   shaking the culture for at least 3 days at ambient temperature; and
   collecting the fungal mycelia from the medium by centrifugation.

7. A method according to claim 6 further comprising lysing said centrifuged fungal mycelia, extracting fungal DNA from said lysed mycelia with an organic solution and precipitating said extracted DNA.

8. A method according to claim 1 comprising detecting the presence of said amplified DNA by staining for photography.

9. A method of isolating DNA of the fungus L. maculans suitable for amplification by polymerase chain reaction from plant tissue infested by said fungus, comprising:
   placing surface-disinfested tissue in liquid fungal minimal medium,
   shaking the culture for at least 3 days at ambient temperature; and
   collecting the fungal mycelia from the medium by centrifugation and isolating DNA from the fungal mycelia.

10. A method according to claim 9 wherein said centrifuged fungal mycelia are lysed and DNA in said mycelia are extracted with an organic solvent and then precipitated.

11. A method according to claim 9 wherein said liquid fungal minimal medium contains $NO_3^-$ as a source of nitrogen.

12. A synthetic oligonucleotide having a sequence selected from the group consisting of:

5'-GCGCTATTACACATGCCTAACAGG-3' [SEQ ID NO:1];

5'-TCCTCTATGCTAAGCTAGCTGTGC-3' [SEQ ID NO:2];

5'-GCGTAAGAAGCGTGCCTTAGAGTC-3' [SEQ ID NO:7];

5'-TCCTGCTCCTACTCCTTCTCTAGC-3' [SEQ ID NO:8];

5'-GGTAGAGCTAGAGGAGGTAGATAA-3' [SEQ ID NO:9]; and

5'-GCACTTATAGAGCCTCCTAGTAGT-3' [SEQ ID NO:10].

13. A set of oligonucleotide primers for polymerase chain reaction amplification of DNA of virulent strains of *L. maculans*, selected from the group consisting of:

(A) 5'-GCGCTATTACACATGCCTAACAGG-3' [SEQ ID NO:1],

5'-TCCTCTATGCTAAGCTAGCTGTGC-3' [SEQ ID NO:2];

(D) 5'-GCGTAAGAAGCGTGCCTTAGAGTC-3' [SEQ ID NO:7],

5'-TCCTGCTCCTACTCCTTCTCTAGC-3' [SEQ ID NO:8];

and (E) 5'-GGTAGAGCTAGAGGAGGTAGATAA-3' [SEQ ID NO:9],

5'-GCACTTATAGAGCCTCCTAGTAGT-3' [SEQ ID NO:10].

14. A diagnostic test kit for testing for infestation of plant tissue by a virulent strain of the fungus *Leptosphaeria maculans*, comprising:

a solution of effective primers which specifically hybridizes to LMR1 [SEQ ID NO:11], a repetitive element of *L. maculans* specific to virulent strains, suitable for amplification of sequences of DNA of said strains by polymerase chain reaction (PCR);

a solution of a buffer suitable for the PCR;

a solution of deoxynucleotides;

DNA from a highly virulent strain of the fungus as a first control;

DNA from a weakly virulent strain of the fungus as second control; and instructions for use of the kit to carry out the PCR on test DNA extracted from plant tissue, followed by detection of amplified DNA produced by the PCR.

* * * * *